(12) United States Patent
Belkin et al.

(10) Patent No.: US 10,363,169 B2
(45) Date of Patent: Jul. 30, 2019

(54) SYSTEM AND METHOD FOR TREATING AN EYE

(71) Applicants: Ramot at Tel-Aviv University Ltd., Tel Aviv (IL); Tel Hashomer Medical Research Infrastructure and Services Ltd., Tel Hashomer (IL)

(72) Inventors: Michael Belkin, Givat Shmuel (IL); Mordechai Goldenfeld, Tel Aviv (IL)

(73) Assignees: TEL HASHOMER MEDICAL RESEARCH INFRASTRUCTURE AND SERVICES LTD., Ramat Gan (IL); RAMOT AT TEL-AVIV UNIVERSITY LTD., Tel Aviv (IL)

(*) Notice: Subject to any disclaimer, the term of this patent is extended or adjusted under 35 U.S.C. 154(b) by 0 days.

(21) Appl. No.: 13/669,961

(22) Filed: Nov. 6, 2012

(65) Prior Publication Data
US 2013/0123761 A1 May 16, 2013

Related U.S. Application Data

(63) Continuation-in-part of application No. PCT/IL2011/000373, filed on May 9, 2011.
(Continued)

(51) Int. Cl.
*A61F 9/007* (2006.01)
*A61F 9/008* (2006.01)
*A61B 18/18* (2006.01)

(52) U.S. Cl.
CPC ............ *A61F 9/0079* (2013.01); *A61F 9/008* (2013.01); *A61F 9/00817* (2013.01); *A61F 9/007* (2013.01);
(Continued)

(58) Field of Classification Search
CPC .. A61F 9/00781; A61F 9/007; A61F 9/00821; A61F 9/008; A61F 2009/00872;
(Continued)

(56) References Cited

U.S. PATENT DOCUMENTS 2,635,502 A 4/1953 Richards
3,594,072 A 7/1971 Feather et al.
(Continued)

FOREIGN PATENT DOCUMENTS

CN 201537172 U 8/2010
DE 202016006265 U1 3/2017
(Continued)

OTHER PUBLICATIONS

Smith et al., "Light Scatter From the Central Human Cornea", Eye, vol. 4 pp. 584-588, 1990.*
(Continued)

*Primary Examiner* — Gary Jackson
*Assistant Examiner* — Sebastian X Lukjan
(74) *Attorney, Agent, or Firm* — Kligler & Associates

(57) ABSTRACT

A system and method are presented for use in delivering electromagnetic radiation to a limbal area of an eye, for example for treatment of glaucoma. The system includes an illumination unit, a beam shaping device and a control unit. The illumination unit includes a first source of electromagnetic radiation configured and operable for producing a beam of electromagnetic radiation having first optical properties to be delivered to the limbal area of a patient's eye to interact therewith and produce a desired effect, and a second source of electromagnetic radiation configured and operable for producing a beam of electromagnetic radiation having second optical properties. The beam shaping device when accommodated in an optical path of said first and second beams defines one or more regions along a path substantially
(Continued)

aligned with a limbus of the patient's eye. The control unit is configured and operable for operating the illumination unit in first and second illumination modes, such that in the first illumination mode the second beam propagates towards said beam shaping device and upon identifying that the second beam illuminates the limbus, the second illumination mode is activated in which the first beam is directed via said beam shaping device to pass through said one or more regions along said path to thereby interact with the limbus.

12 Claims, 5 Drawing Sheets

Related U.S. Application Data

(60) Provisional application No. 61/332,994, filed on May 10, 2010.

(52) U.S. Cl.
CPC ....... A61F 9/00781 (2013.01); A61F 9/00804 (2013.01); A61F 9/00821 (2013.01); A61F 2009/0087 (2013.01); A61F 2009/00872 (2013.01); A61F 2009/00887 (2013.01); A61F 2009/00891 (2013.01)

(58) Field of Classification Search
CPC ........ A61F 9/00804; A61F 2009/00887; A61F 2009/0087
USPC .................................................. 606/4, 5, 6
See application file for complete search history.

(56) References Cited

U.S. PATENT DOCUMENTS

| | | | |
|---|---|---|---|
| 4,641,349 A | | 2/1987 | Flom et al. |
| 4,718,418 A | | 1/1988 | L'Esperance |
| 5,152,760 A | * | 10/1992 | Latina ..................... A61F 9/008 606/6 |
| 5,370,641 A | * | 12/1994 | O'Donnell, Jr. ........ A61F 9/008 128/898 |
| 5,479,222 A | | 12/1995 | Volk et al. |
| 5,549,596 A | | 8/1996 | Latina |
| 5,598,007 A | | 1/1997 | Bunce et al. |
| 5,865,830 A | | 2/1999 | Parel et al. |
| 6,033,396 A | | 3/2000 | Huang et al. |
| 6,059,772 A | | 5/2000 | Hsia et al. |
| 6,096,029 A | * | 8/2000 | O'Donnell, Jr. ..... A61B 18/203 606/3 |
| 6,099,521 A | * | 8/2000 | Shadduck .................. 606/4 |
| 6,099,522 A | | 8/2000 | Knopp et al. |
| 6,146,375 A | * | 11/2000 | Juhasz ............... A61F 9/00825 606/5 |
| 6,210,399 B1 | * | 4/2001 | Parel ....................... A61F 9/008 606/10 |
| 6,258,082 B1 | * | 7/2001 | Lin ................................. 606/5 |
| 6,263,879 B1 | * | 7/2001 | Lin ......................... A61F 9/008 128/898 |
| 6,319,274 B1 | * | 11/2001 | Shadduck ............. A61N 5/0613 606/13 |
| 6,325,792 B1 | | 12/2001 | Swinger et al. |
| 6,454,763 B1 | | 9/2002 | Motter et al. |
| 6,514,241 B1 | * | 2/2003 | Hsia et al. ........................ 606/6 |
| 6,530,916 B1 | | 3/2003 | Shimmick |
| 6,616,275 B1 | * | 9/2003 | Dick .................... A61B 3/1015 351/212 |
| 6,673,062 B2 | | 1/2004 | Yee et al. |
| 6,685,317 B2 | | 2/2004 | Su et al. |
| 6,698,886 B2 | | 3/2004 | Pollack et al. |
| 6,736,806 B2 | | 5/2004 | Ruiz et al. |
| 6,979,328 B2 | | 12/2005 | Baerveldt et al. |
| 7,282,046 B2 | | 10/2007 | Simon |
| 7,792,249 B2 | | 9/2010 | Gertner et al. |
| 8,109,635 B2 | | 2/2012 | Allon et al. |
| 8,442,185 B2 | | 5/2013 | Gertner et al. |
| 8,568,393 B2 | | 10/2013 | Palanker |
| 8,630,388 B2 | | 1/2014 | Gertner et al. |
| 8,679,100 B2 | | 3/2014 | Raksi et al. |
| 8,771,261 B2 | | 7/2014 | Andersen et al. |
| 9,220,407 B2 | | 12/2015 | Yam et al. |
| 9,622,911 B2 | | 4/2017 | Rubinfeld et al. |
| 2003/0109907 A1 | | 6/2003 | Shadduck |
| 2004/0215175 A1 | * | 10/2004 | Feklistov ................ A61F 9/008 606/4 |
| 2005/0096639 A1 | * | 5/2005 | Slatkine et al. ................... 606/5 |
| 2005/0107774 A1 | | 5/2005 | Lin |
| 2005/0254009 A1 | | 11/2005 | Baker et al. |
| 2005/0286019 A1 | | 12/2005 | Wiltberger et al. |
| 2005/0288745 A1 | | 12/2005 | Andersen et al. |
| 2007/0081166 A1 | | 4/2007 | Brown et al. |
| 2007/0129709 A1 | | 6/2007 | Andersen et al. |
| 2007/0159600 A1 | | 7/2007 | Gil et al. |
| 2007/0213693 A1 | * | 9/2007 | Plunkett ........................... 606/6 |
| 2008/0089481 A1 | | 4/2008 | Gertner |
| 2008/0108934 A1 | | 5/2008 | Berlin et al. |
| 2008/0161781 A1 | * | 7/2008 | McArdle ............. A61F 9/00802 606/6 |
| 2008/0319427 A1 | * | 12/2008 | Palanker ................ A61F 9/008 606/4 |
| 2009/0157062 A1 | | 6/2009 | Hauger et al. |
| 2010/0076419 A1 | | 3/2010 | Chew et al. |
| 2010/0324543 A1 | | 12/2010 | Kurtz et al. |
| 2011/0144627 A1 | | 6/2011 | Smith et al. |
| 2012/0083772 A1 | | 4/2012 | Rubinfeld et al. |
| 2012/0089134 A1 | * | 4/2012 | Horvath ............. A61F 9/00825 606/6 |
| 2012/0283557 A1 | | 11/2012 | Berlin |
| 2013/0204236 A1 | | 8/2013 | Awdeh |
| 2013/0289450 A1 | | 10/2013 | Homer |
| 2014/0094785 A1 | | 4/2014 | Charles |
| 2014/0135753 A1 | | 5/2014 | Feklistov et al. |
| 2014/0307077 A1 | | 10/2014 | Prabhakar |
| 2015/0223683 A1 | | 8/2015 | Davidovics et al. |
| 2015/0313759 A1 | | 11/2015 | Vera et al. |
| 2016/0008172 A1 | | 1/2016 | Kahook et al. |
| 2016/0113816 A1 | | 4/2016 | Herekar et al. |
| 2017/0087014 A1 | | 3/2017 | Potter, Jr. et al. |
| 2017/0360604 A1 | | 12/2017 | Bach et al. |

FOREIGN PATENT DOCUMENTS

| | | |
|---|---|---|
| EP | 0224322 A1 | 6/1987 |
| EP | 3224322 | 6/1987 |
| EP | 0651982 | 5/1995 |
| EP | 0651982 A1 | 5/1995 |
| FR | 2655837 A1 | 6/1991 |
| WO | 9216259 A1 | 10/1992 |
| WO | 2007103349 A2 | 9/2007 |
| WO | 2008112236 A1 | 9/2008 |
| WO | 2011085274 A1 | 7/2011 |

OTHER PUBLICATIONS

Barkana Y. et al., "Selective Laser Trabeculoplasty", Survey of Ophthalmology, vol. 52, No. 6, pp. 634-653, 2007.
Ivandic, Boris T. et al., "Early Diagnosis of Ocular Hypertension Using a Low-Intensity Laser Irradiation Test", Photomedicine and Laser Surgery, vol. 00, No. 00, pp. 1-5, 2009.
U.S. Appl. No. 13/696,867, filed Dec. 16, 2013.
International Application PCT/IB2014/058973 Search Report dated Jun. 22, 2014.
U.S. Appl. No. 13/696,867 Office Action dated Oct. 10, 2014.
CN Application # 2014800101570 Office Action dated May 17, 2016.
European Application # 14757324.0 search report dated Oct. 11, 2016.
Nozaki et al., "Patterned Laser Trabeculoplasty with PASCAL streamline 577", Investigative Ophthalmology & Visual Science, vol. 54, p. 1867, Jun. 2013.

(56) References Cited

OTHER PUBLICATIONS

Turati et al., "Patterned Laser Trabeculoplasty", Ophthalmic Surgery, Lasers and Imaging, vol. 41, No. 5, pp. 538-545, 2010.
U.S. Appl. No. 14/765,862 office action dated Jan. 30, 2018.
U.S. Appl. No. 14/765,862 office action dated Oct. 25, 2018.
EP Application # 11724805.4 office action dated Sep. 7, 2017.
JP Application # 2015-558576 office action dated Oct. 25, 2017.

* cited by examiner

SYSTEM AND METHOD FOR TREATING AN EYE

FIELD OF THE INVENTION

This invention relates to medical devices, and in particular to such devices for use in ophthalmology.

BACKGROUND OF THE INVENTION

The following documents are considered to be relevant for an understanding of the background of the invention:

Barkana, Y and Belkin M., Selective Laser Trabeculoplasty, Survey of Ophthalmology 52:634-653, 2007.

U.S. Pat. No. 6,698,886 to Pollack et al.

U.S. Pat. No. 5,479,222 to Volk.

Under normal circumstances, aqueous humor is secreted the posterior chamber of the eye, and then circulates through the pupil into the anterior chamber where it passes through the trabecular meshwork, before being secreted from the eye. In most forms of glaucoma, the flow of the aqueous humor through the trabecular meshwork is impeded, preventing adequate drainage of the aqueous humor from the eye. This leads to a rise in the intraocular pressure, a state which may cause damage to the eye and lead to progressive blindness. One method to treat or prevent this from occurring is to alter some of the trabecular meshwork in order to improve the flow of aqueous humor through the trabecular meshwork.

A common method of enhancing the flow of aqueous humor through the trabecular meshwork is laser trabeculoplasty (LTP) which consists of the application of laser energy to the trabecular meshwork. There are a several types of LTP, such as selective laser trabeculoplasty (SLT) argon laser trabeculoplasty (ALT), diode laser trabeculoplasty (DLT), micropulse laser trabeculoplasty (MLT), and titanium: sapphire laser trabeculoplasty (TLT). The various types of LTP differ in the wavelength and other characteristics of the laser beam. SLT, for example, utilizes a Q-switched 532 Nd:YAG laser which selectively targets melanin-containing cells within the trabecular meshwork. (Barkana, Y et al) While the entire mechanism of action has not been completely elucidated, it is believed that laser-stimulated melanin-containing cells release cytokines which attract other cell types to the trabecular meshwork that increase its permeability. Unlike older versions of LTP, such as ALT, selective laser trabeculoplasty does not require precise targeting since the wavelength and energy of the light used selectively targets the melanine containing cells within the meshwork. The surrounding cells are not heated or destroyed. Thus, the fluid outflow is improved without damaging the trabecular meshwork. SLT has been used to treat primary open angle glaucoma, intraocular hypertension, normal tension glaucoma, aphakic (glaucoma in patients without a natural lens in their eye), pseudophakic glaucoma (glaucoma in patients without an artificial lens in their eye pigmentary, chronic angle closure glaucoma and juvenile glaucoma. SLT has also been successfully used to treat pressure increases in the eye caused by certain medications.

FIG. 1 shows the treatment of an eye 1 by LTP. Eye drops are first placed in the eye to provide surface anesthesia and to prepare the eye for the procedure. The trabecular meshwork 10 is situated around the angle of the anterior chamber of the eye and is not directly observable because it is obscured by the limbal area 12. A gonioscopic contact lens 2 which includes a mirror 3 is applied to the eye 1 to direct a laser beam 6 through the cornea S to the trabecular meshwork 10 underneath the limbal area 12. Typically, between 180° to 360° of the anterior chamber angle is irradiated by rotating the gonioscopic contact lens 12 after each laser pulse. About 100 laser pulses of a few nanoseconds duration and about 0.6 to 200 mJ of energy are delivered to the trabecular meshwork.

U.S. Pat. No. 5,479,222 to Volk discloses a gonioscopic lens system comprising at least two lenses. At least one of the lenses includes an aspheric surface of revolution. The lenses are positioned adjacent one another in a housing, such that the refractive properties of each are combined to converge light from an illumination light source to the entrance pupil of the patient's eye to illuminate the fundus. The lens system is designed for use with an associated ophthalmoscopic lens, enabling selective modification of the optical characteristics of the ophthalmoscopic lens system in a predetermined manner.

U.S. Pat. No. 6,698,886 to Pollack et al discloses an iridotomy and trabeculoplasty goniolaser lens having a contact lens element, a planar mirror offset from the optical axis of the contact lens element and first and second button lenses mounted on the anterior surface of the contact lens element. Magnification, curvature and location of the button lenses are chosen so as to provide the ability to simultaneously deliver laser energy to the iris of a patient's eye along a first optical path offset from the optical axis of the contact lens element and to view the trabecular meshwork around the region where the laser energy was applied.

Irradiating the trabecular meshwork with a laser beam directed through the cornea, as shown in FIG. 1, is often not possible in cases of narrow or closed angle glaucoma which occurs when the iris of the eye approaches the cornea and thus narrows or eliminates the angle between the cornea and the iris. This is the most common type of glaucoma in Chinese and Indian people and hence the commonest form of glaucoma and blindness in the world. In these cases, the laser beam cannot reach the trabeculum meshwork to be irradiated.

SUMMARY OF THE INVENTION

The present invention is based on the novel and unexpected finding that LTP can be performed by irradiating the trabecular meshwork through the limbal area without a need for any contact with the eye, thus avoiding the need for a gonioscopic contact lens. The inventors have found that irradiating the trabecular meshwork directly through the limbal area can achieve results comparable to those obtained by prior art LTP methods that utilize a gonioscopic contact lens. The inventors have found, for example, that a 532 nm laser beam is capable of penetrating the 1 mm thick limbal area and reaching the trabecular tissue to be treated with an adequate intensity to enhance the flow of aqueous humor through the trabecular meshwork, and to cause a significant decrease in intraocular pressure.

Thus, for example, in one patient suffering from open angle glaucoma with pseudoexfoliation, following irradiation of the limbal area with a 532 nm Nd:YAG laser (total energy delivered to a single eye around 10 J), the intraocular pressure reduced within a day from 24 to 14 mmHg while the patient was using antihypertensive eye drops. In another patient suffering from open angle glaucoma with pseudoexfoliation, the intraocular pressure decreased from 24 mmHg to 12 mmHg a week after treatment with a reduction of antihypertensive eye drops from 3 to 2. In a patient with primary open angle glaucoma the intraocular pressure was reduced from 27 to 18 mm Hg following the treatment.

Thus, in one of its aspects, the present invention provides a beam shaping device for directing one or more treatment beams of electromagnetic radiation to one or more regions located on the limbal area of an eye. To this end, the device is preferably also configured for directing an aiming (guiding) beam towards the patient's eye. The configuration is such that the aiming beam creates an illuminated pattern on the eye defining a boundary substantially matching the limbal area, thus enabling the treatment beam(s) to be incident onto the region(s) of the limbal area. The aiming and treatment beams are typically in the visual and NIR spectra respectively. The aiming beam allows a physician to visually control the correct location of the illuminated pattern and accordingly to match between its boundary and the limbal area of the eye.

The device of the invention comprises a thin substantially circular (e.g. circular or oval-like) plate having one aperture or an array of apertures that are arranged in a spaced apart relationship along the peripheral region of the plate to overly locations around the limbal area. The apertures may have, for example, a circular cross section or an arched shape. It should be understood that apertures actually present optical windows which may be implemented as holes/perforations or regions of a desirably transmitting material. Thus apertures, having circular or arched cross-section, are transparent to electromagnetic radiation of the treatment beams of interest and allow them to pass through, while the rest of the plate is opaque to these beams. The plate with one or more apertures may be rotatable so that each aperture/transparent region can be positioned over different locations of the scleral limbus while scanning the limbal area. Alternatively, the plate may have a ring-like aperture along the periphery of the plate, in which case the treatment beam has an annular shape.

As indicated above, the plate in the regions outside the aperture(s) is opaque for the electromagnetic radiation of the treatment beam(s). As for the electromagnetic radiation of the aiming beam (i.e. visual spectrum), the configuration may be such that the plate is transparent for this radiation, thus illuminating a circular spot with its outer boundary substantially coinciding with the limbal area, i.e. being of a slightly larger diameter such that the periphery region of the plate in which the aperture(s) is/are located is aligned with the limbal area.

Alternatively, the plate in the regions outside the aperture (s) may be opaque for visual spectrum as well. In this case the aiming beam has either equal or larger diameter as compared to that of the plate and illuminates a ring-like region on the eye in the form of a circular array of small spots corresponding to the array of apertures, where the diameter of the ring-like region (or at least an inner diameter thereof) substantially coincides with the limbal area. As for the treatment radiation, it may also be in the form of a beam directed along the same optical path as the aiming beam, i.e. directed towards the illuminated pattern created by the aiming beam upon identifying that the pattern surrounds the limbal area (e.g. by manipulating the plate location and accordingly the aiming beam propagation axis).

As indicated above, the device needs not be placed directly onto the eye being treated, and thus may be configured to be held a predetermined distance away from the eye.

In another of its aspects, the invention provides a system for treating an eye. The system of the invention includes an illumination unit including first and second sources of electromagnetic radiation producing first and second beams having first and second optical properties for respectively treating and beam aiming purposes. Also provided in the system is the above-described beam shaping device for accommodating in an optical path of the first and second beams for directing the aiming beam so as to align it with the limbus and direct the treatment beam to one or more regions along the circumference of the limbal area as "marked" by the aiming beam. The electromagnetic radiation may have a wavelength in the visible spectrum and in the near infrared spectrum between 514 and 850 nm, for example using a 532 Nd:YAG laser.

It should be understood that, generally, the source of electromagnetic radiation may include a broadband emitter in which case an appropriate spectral filter arrangement is used for selectively passing beams of the visible and near infrared ranges. Practically, the source of electromagnetic radiation includes two different emitters of electromagnetic radiation, one for generating radiation in the visible light range (aiming beam) and the other for generating radiation in the near infrared range (treatment beam), between 514 and 850 nm. The visible light beam is used to confirm that the treatment optical path hits the points of interest at the limbal area of the eye and then the second source is activated to deliver the treating beam along said path to interact with these points. The system may be configured to generate pulses of the electromagnetic radiation. In this case, the pulses of the treatment beam may be between 1 to 1000 msec in duration, and the fluence of a single pulse may be 0.5 to 1 $J/cm^2$. The total energy delivered to a single eye may be from 4 to 8 J.

It should be noted that the present invention advantageously provides remarkably short duration of the treatment procedure. The treatment performed by the technique of the invention takes less than a second to complete while having an immediate and long lasting effect on the treatment process of glaucoma, thus enhancing the patient convenience and providing an effective treatment. This is due to the fact that the treatment beam may be quickly and precisely delivered to the treatment area and this condition may be accurately maintained during the treatment, thus allowing the treatment to be quick and with the desirably high light intensity and energy as regions outside the treatment area are prevented from being reached by the treatment beam.

Thus, according to the broad aspect of the invention, there is provided a system for use in delivering electromagnetic radiation to a limbal area of an eye. The system comprises:

(a) an illumination unit comprising a first source of electromagnetic radiation configured and operable for producing a beam of electromagnetic radiation having first optical properties to be delivered to the limbal area of a patient's eye to interact therewith and produce a desired effect, and a second source of electromagnetic radiation configured and operable for producing a beam of electromagnetic radiation having second optical properties;

(b) at least one beam shaping device for accommodating in an optical path of said first and second beams, said beam shaping device being configured and operable such that when in said optical path, it defines one or more regions along a path substantially aligned with a limbus of the patient's eye; and (c) a control unit connected to the illumination unit and configured and operable for operating the illumination unit in first and second illumination modes, such that in the first illumination mode the second beam propagates towards said beam shaping device and upon identifying that the second beam illuminates the limbus, the second illumination mode is activated in which the first beam is directed via said beam shaping device to pass through said one or more regions along said path to thereby interact with the limbus.

As indicated above, the beam shaping device may comprise a disk-like plate. According to some embodiments, the disk-like plate is made of a material substantially opaque for at least the first (treatment) beam and is formed with a pattern of the one or more regions configured as optical windows transparent for the first (treatment) and second (aiming) beams. The pattern defines the illumination path along a circumference of the disk-like plate. The disk-like plate may be made of the material substantially opaque for both the first and second beam.

The circumferential path is preferably located at a periphery of the disk-like plate.

The interaction between the first beam and the beam shaping device (e.g. the optical windows in the opaque disk-like plate) splits the first beam into a predetermined number of light components corresponding to a number of said regions along the illumination path.

In some embodiments, a set of the beam shaping devices is used, each beam shaping device comprising a disk-like plate described above. The disk-like plates of the set are configured with different diameters of the illumination paths.

In some embodiments, the pattern of said regions/optical windows (transparent for the first and second beams) includes an array of such regions arranged in a spaced-apart relationship along a circumferential path on the disk corresponding to the illumination path.

In some other embodiments, the beam shaping device comprises a disk-like plate opaque for at least the first beam and is formed with the region transparent for both beams, where this region has an annular shape along a circumferential path on the disk corresponding to the illumination path.

As indicated above, the first source produces treatment radiation (typically in the NIR spectrum), while the second source produces radiation in the visual spectrum. The control unit may operate the first source, as well as a second source, in a pulse mode.

It should be noted that the disk-like plate of the beam shaping device may be mounted for controllable rotation with a predetermined rate thereby providing fir scanning the limbus by the treatment beam passing through said region(s)/optical window(s).

According to another aspect of the invention, there is provided a method for delivering electromagnetic radiation to a limbal area of an eye, e.g. treatment of glaucoma. The method comprises:
  delivering electromagnetic radiation to the limbal area of
    a patient's eye wherein the electromagnetic radiation is
    in the form of first and second beams, the first beam
    being a beam of visual spectrum and the second beam
    being of electromagnetic radiation having optical properties such that interaction of the second beam with the
    eye at the limbus causes desired treatment effect;
    wherein said delivering comprises:
    directing the first visual beam towards the eye via, a
      predetermined illumination path while manipulating
      a location of the illumination path with respect to the
      eye;
    upon identifying that the first beam illuminates the
      limbus, directing the second beam towards the eye
      via one or more regions along said illumination path
      to thereby cause interaction of the second beam with
      the eye essentially at the limbus.

The invention also provides an ensemble (set) comprising two or more beam shaping devices of the invention for delivering electromagnetic radiation to a limbal area of an eye. In the ensemble of the invention, each of the two or more beam shaping devices produces a circular/cylindrical array of emitted treatment beams, such that the circular/cylindrical array produced by one device has different diameter than that produced by another device. Considering the use of an aperture/windowed plate described above, such devices utilize plates of different diameters. Similarly, two or more devices may produce arrays of emitted beams having a cross sectional shape of a circular arc of different diameters. The ensemble may also include two or more devices each producing a beam having an annular cross section of one or both of a different inner diameter and/or a different outer diameter.

The ensemble of the invention may be used when it is desirable to irradiate the limbal area of an eye in a procedure using a series of irradiations of different geometrical parameters. Thus, for example, the eye may first be irradiated with either a cylindrical array of circular beams or beams having a cross sectional shape of a circular arc wherein the cylindrical array or the circular arcs have a relatively small diameter (e.g. 9 mm), and then be irradiated one or more additional times, each time increasing the diameter. The final diameter may be around 13 mm. Similarly, the eye may be sequentially irradiated with a series of beams having an annular cross section where one or both of the inner diameter and the outer diameter increases each time.

In still another aspect, the present invention provides a method for treating an eye. The method of the invention comprises directing electromagnetic radiation to one or more locations on the sclera limbus of an eye. The electromagnetic radiation may have wavelengths in the visible and near infrared range, between 514 and 850 nm, and may be generated, for example, using a 532 Nd:YAG laser. The treatment electromagnetic radiation may be delivered to the limbal area in pulses. In this case, the pulses may be between 1 to 1000 millisecond in duration, and the fluence of a single pulse may be 0.5 to 1 J/cm$^2$. The total energy delivered to a single eye may be from 4 to 8 J. The method of the invention may be carried out using the system of the invention.

The invention may be used in the treatment of narrow or closed angle glaucoma, since, in accordance with the invention, the beam of electromagnetic radiation is not directed through the angle of the anterior chamber of the eye.

In the device of the invention, when the emitted radiation comprises two or more emitted beams that are arrayed in a cylindrical array, the cylindrical array may have a circular cross section having a diameter from 9 to 13 mm. When the emitted radiation comprises an array of one or more beams having a cross sectional shape of a circular arc, the circular arc may have a diameter from 9 to 13 mm. When the emitted radiation comprises an array comprising a beam having an annular cross section, the annular cross section may have an inner diameter and an outer diameter, the average of the inner diameter and the outer diameter being from 9 to 13 mm.

When the emitted radiation comprises two or more emitted beams that are arrayed in a cylindrical array, the device may comprise an element opaque to the electromagnetic radiation having therein a circular array of apertures (constituting optical windows) extending from a first face of the opaque element to a second face of the opaque element (for simplicity, wherever "apertures" is mentioned it also means transparent regions to the specific radiation used). The circular array of apertures may comprise, for example, at least 50 apertures. The opaque element may be rotatable about the center of the circular array. When the emitted radiation comprises an array of one or more beams having a cross sectional shape of a circular arc; the device may comprise an element opaque to the electromagnetic radiation having therein a circular array of apertures, each aperture having a cross sectional shape of a circular arc and each aperture extending from a first face of the opaque element to a second face of the opaque element. The opaque element may be rotatable about the center of the circular array. When the emitted radiation comprises two or more emitted beams that are arrayed in a cylindrical array, the device may comprise a cylindrical array of optic fibers. The cylindrical array of optic fibers may be embedded in an opaque element, with the cylindrical array of optic fibers extending from a first face of the opaque element to a second face of the opaque element. When the emitted radiation comprises a beam having an annular cross section, the device may comprise a refractive or diffractive optical element. When the emitted radiation comprises a beam having an annular cross section, the device may comprise an ellipsoidal mirror.

As mentioned above, the device of the invention needs no contact with the eye for the device operation. If, however, the device of the invention operates in the contact mode, i.e. contacts the eye, the device may comprise a concave outer surface. The concave surface may conform to the surface of the eye to promote stabilization of the device on an eye.

In the system of the invention, the first source may be a laser. The laser may have, for example, a wavelength from 514 to 850 nm. The laser may be, for example, a 532 Nd:YAG laser.

The system may further comprise a control unit configured to execute a predetermined regime of activation of the first, as well as second, source of electromagnetic radiation. The predetermined regime of activation of the source(s) of electromagnetic radiation may comprise a series of pulses.

BRIEF DESCRIPTION OF THE DRAWINGS

In order to understand the invention and to see how it may be carried out practice, embodiments will now be described, by way of non-limiting example only, with reference to the accompanying drawings, in which.

DETAILED DESCRIPTION OF EMBODIMENTS

Figure 1:
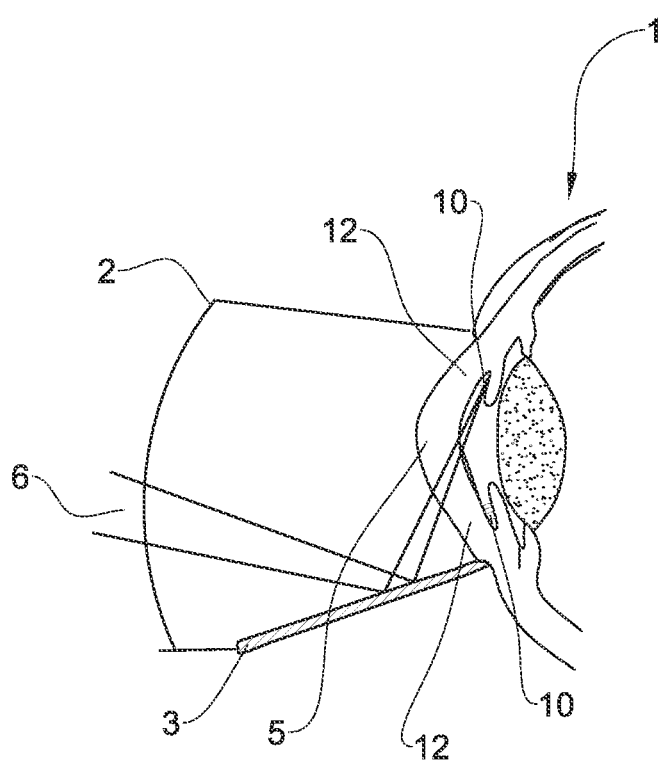
FIG. 1 shows the beam path in SLT using a gonioscopy contact lens.

FIG. 1 illustrates schematically the beam path in the conventional SLT using a gonioscopy contact lens.

The following are several examples of a device of the present invention for crating structured treatment light shaped for interacting with multiple regions along a limbal area of an eye, while being guided towards the regions of the limbal area by aiming light of a different spectral range. These examples utilize masking of the light propagation path and/or optical light directing elements.

Figure 2:
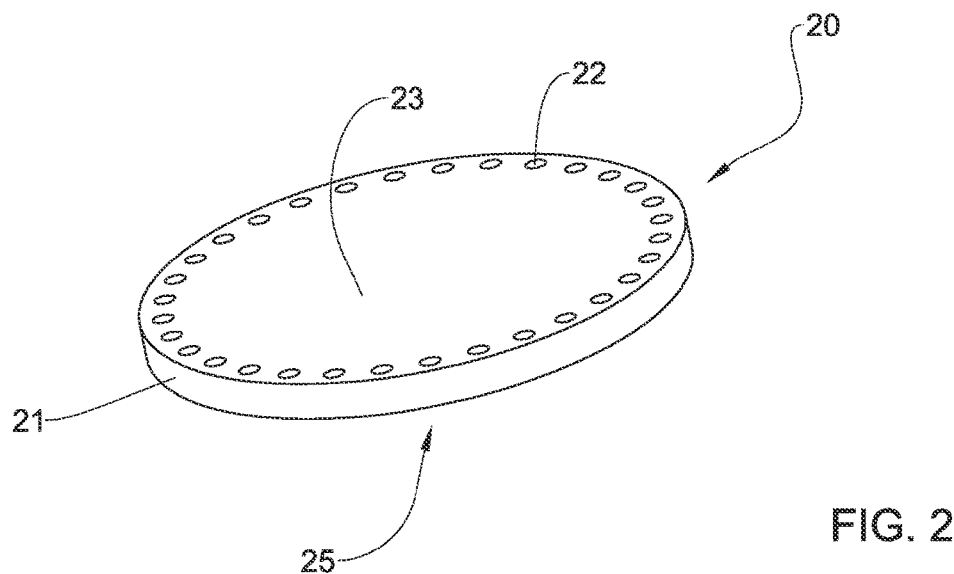
FIG. 2 shows a device for directing electromagnetic radiation to one or more regions of a limbal area of an eye having a circular array of spaced-apart apertures, in accordance with one embodiment of the invention.

Reference is made to FIG. 2 which shows an example of a device 20 of the present invention for directing electromagnetic radiation to one or more regions of a limbal area of an eye. The device 20 includes a thin plate 21 that may be a circular disk (or generally "substantially circular" or "circular-like" disk). The plate 21 is provided with at least one aperture (generally, an optical window), a plurality of such small apertures 22 are exemplified in FIG. 2 that may have a circular cross section. In this non-limiting example, the plate 21 is formed from an opaque material such as metal. The apertures 22 are in the form of through-going openings that pass through the plate 21 from an upper surface 23 to a bottom surface 25. It should be noted that the apertures 22 may be equivalently substituted by regions in the plate that are made from material which is transparent to the beam in use. Thus, electromagnetic radiation incident onto the plate will transverse the plate only at the apertures 22. The apertures 22 are arranged in a circular array, i.e. are arranged in a spaced-apart relationship along a circular path, along a periphery region of the plate 21 such that when the device is in operation the apertures overly/are aligned with the sclera limbus of an eye being treated. The circular array of apertures may have a diameter in the range from 11 to 13 mm, which is the typical diameter of the sclera limbus. The plate 21 may have as many as 200 apertures (equally) spaced along the peripheral circumference of the plate 21, so that 200 spots in the sclera limbus can be treated simultaneously.

The beams that interact with the sclera limbus through the apertures are treatment beams, which are of a NIR wavelength range. In order to direct the treatment beams to the regions of the sclera limbus, an aiming/guiding beam is used. This aiming beam is of a wavelength in the visual spectrum, having smaller intensity (reduced-energy) as compared to the treatment beam and serves only for properly aiming the treatment beam. The aiming beam is shaped to draw the path along the limbus. Considering the use of the opaque plate as described in the present example, the plate has a diameter corresponding to that of the eye region enclosed by the limbus, and the aiming beam has a cross-section (diameter) substantially of the diameter of the plate thus illuminating an array of small spots through the apertures in the plate 21. By appropriately manipulating the plate position, this array of spots can be aligned with the regions along the whole circumference of the limbus. When the operator sees the aiming beam positioned properly, he activates the treatment illumination. The latter may utilize a single beam which when interacting with the aperture plate becomes split into an array of narrow beams passing through the apertures to the limbus regions; or alternatively the treatment beam may be initially split into an array of beams supplied to the plate by an array of optical fibers. The desired treatment may be achieved by treating discrete regions of the limbus, or if needed the plate may be rotated thus treating the entire lumbus by scanning.

Figure 3:
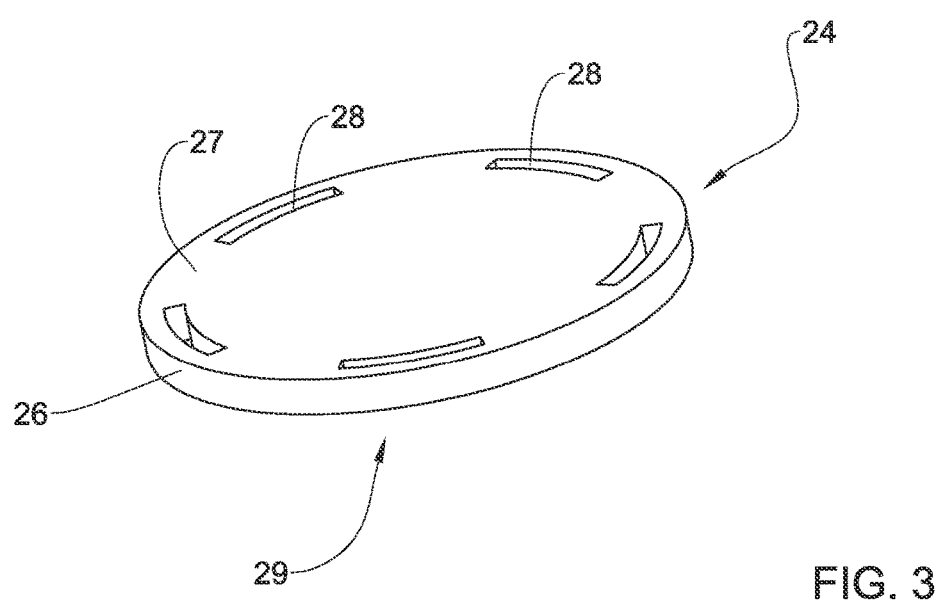
FIG. 3 shows a device for directing electromagnetic radiation to one or more regions of a limbal area of an eye having an array of arc shaped apertures, in accordance with another embodiment of the invention.

FIG. 3 shows a device 24 for directing electromagnetic radiation to one or more regions of a limbal area of an eye in accordance with another embodiment of the invention. The device 24 is generally similar to that of FIG. 2 but with a somewhat different pattern of apertures/optical windows. The device 24 thus comprises a thin plate 26 that may be a circular disk. The plate 26 is provided with a plurality of small apertures 28 which in the present example have the shape of circular arcs. The plate 26 is formed from an opaque material (such as metal) for both treatment and aiming radiation spectra. The apertures 28 pass through the plate 26 from an upper surface 27 to a bottom surface 29. Thus, electromagnetic radiation directed to the plate 26 will transverse the plate only at the apertures 28. The apertures 28 are arranged in a circular array so as to overly the sclera limbus of an eye being treated. The part of the disk 26 defined by the circular path where the apertures are located (periphery region of the disk) may have a diameter in the range from 11 to 13 mm, which is the typical diameter of the sclera limbus. Again, the apertures 28 may be equivalently substituted by regions in the plate that are made from material which is transparent to the beam in use. It should be understood that the aiming beam may be configured and directed as described above with reference to FIG. 2.

Figure 4:
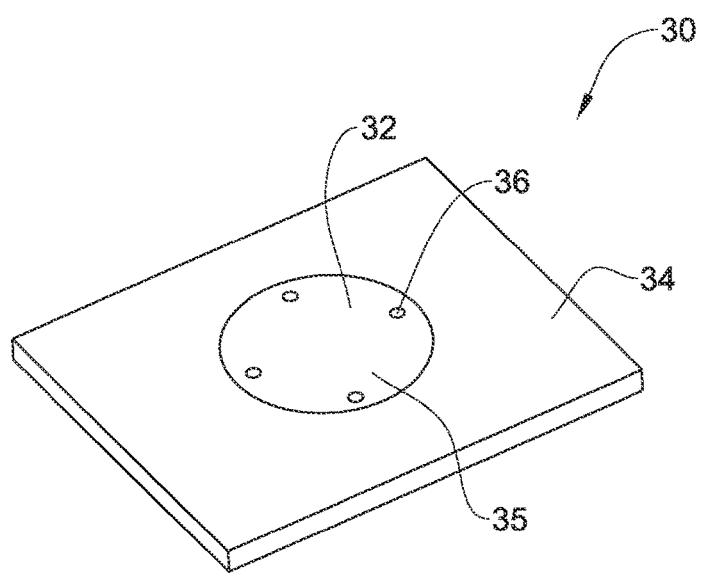
FIG. 4 shows a device for directing electromagnetic radiation to one or more regions of a limbal area of an eye having a circular array of apertures, where the array is rotatable.

FIG. 4 shows a device 30 for directing electromagnetic radiation to one or more regions of a limbal area of an eye in accordance with yet another embodiment of the invention. The device 30 comprises a circular disk/plate 32 that is mounted for rotation in a circular hole in a thin plate 34. The disk 32 is provided with a pattern formed by a plurality of small apertures 36. The plate 32 may have any pattern of apertures, e.g. that of FIG. 2 or 3, or may have a single aperture e.g. of a circular cross section. In the present not limiting example, an array of fours spaced apart circular apertures is shown. The disk 32 is formed from an opaque material such as metal. The apertures 36 pass through the disk 32 from an upper surface 35 to a bottom surface. Thus, electromagnetic radiation directed to the circular disk 32 will transverse the plate only at the apertures 36. The apertures 36 are arranged along a circle to overly the sclera limbus of an eye being treated. The circular array of apertures is located at the periphery of the disk 32 that may have a diameter in the range from 11 to 13 mm, which is the typical diameter of the sclera limbus. The apertures 36 may be equivalently substituted by regions in the plate that are made from material which is transparent to the beam in use. In use, the disk 32 may be rotated with a rotation rate corresponding to that of the pulses of electro-magnetic radiation to deliver the radiation to a number of spots in the sclera limbus that is significantly greater than the number of apertures in the disk. It should be understood that the aiming beam may be configured and directed as described above with reference to FIG. 2.

It should be noted that in any of the above-described examples, the aperture disk/plate may be made of a material transparent for visual spectrum. In this case, the aiming beam may have a diameter substantially equal to or slightly larger than that of the disk, and would illuminate a spot, the boundary of which substantially coincides with the limbus circumference.

Figure 5:
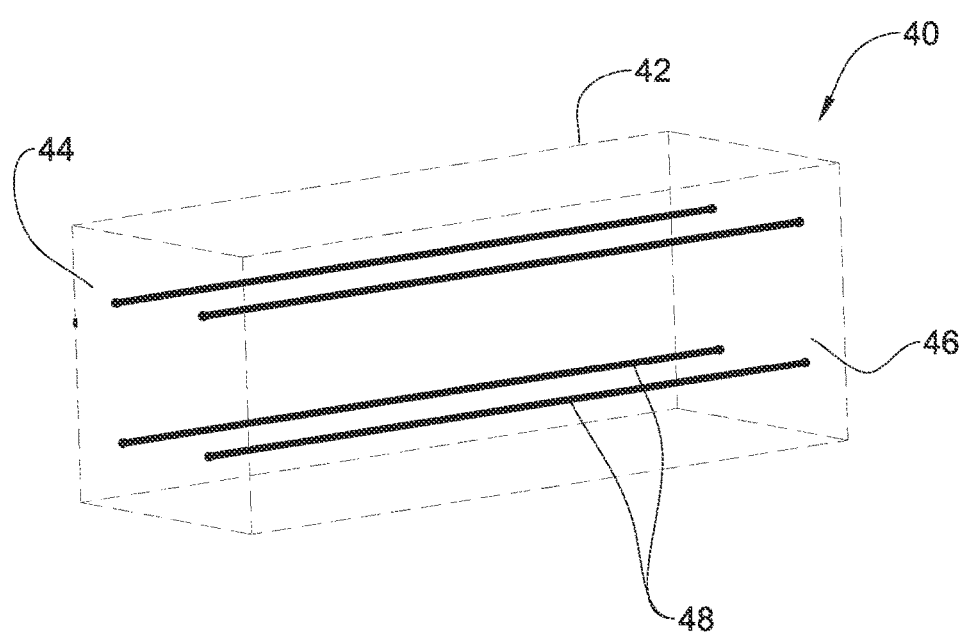
FIG. 5 shows a device for directing electromagnetic radiation to one or more regions of a limbal area of an eye that includes one or more optic fibers arranged in a cylinder.

FIG. 5 shows a device 40 for directing electromagnetic radiation to one or more regions of a limbal area of an eye in accordance with still another embodiment of the invention. In the present example, no aperture disk is used but rather the device 40 includes a block 42 of an opaque material shown in phantom drawing in FIG. 5. The block 32 has a first face 44 and an oppositely situated second face 46. One or more optic fibers 48 are located inside the block and extend from the first face 44 to the second face 46. Thus, electromagnetic radiation directed to the first face 44 will be split into spatially separated beams that transverse the block 42 only along the optic fibers 48. The cross-sectional dimension (diameter) of the block is slightly larger than the limbus area, while the ends of the optic fibers 48 at the output face 46 of the block are arranged in a circular array along a path substantially corresponding to the diameter of the limbus so that the ends of the optic fibers 48 in the second face 46 overly the sclera limbus of an eye being treated. The circular path formed by the ends of the optic fibers 48 at the output face 46 may have a diameter in the range from 11 to 13 mm, which is the typical diameter of the sclera limbus.

It should be understood that, according to the invention, each one of the above-described devices 20, 24, 30 and 40 may be used to define an annulus which covers the limbal area of a patient's eye properly. The annulus is defined by usage of a shaped beam of visible light to direct the operator about where a treating beam will hit the eye, then the operator can activate the treating beam to irradiate the whole annulus or specific spots within the annulus as desired. The treatment of annular region may be achieved by using either a ring-like aperture in the plate or by using one or more apertures and rotation of the plate.

It should be noted, although not specifically shown, that in some other embodiments of the device of the invention, the structured treatment light may be created by using a beam shaping element being a refractive or diffractive optical element. The refractive or diffractive optical element may be made from glass or plastic having transmitting and refracting or diffractive optics which will create a circular beam or rapidly deliver a number of discrete beams to the limbal area. When electromagnetic radiation is incident on the refractive or diffractive optical element, the radiation exits the opposite side of the element as a beam having an annular cross section. This allows irradiation of an annulus around the limbal area by a continuous ring of light. The annulus of light may have, for example, a diameter between 9 and 13 mm, and may be from 0.5 to 2.5 mm in radial width. The lasers involved may be doubled Nd/YAG, argon or any diode emitting radiation in the visible or infrared.

In yet other embodiments of the device of the invention, an ellipsoidal or parabolic mirror can be used that when illuminated by a large spat of light scanning along a large circle generate a small ring at its focal plane.

The optical device may be a lens through which a single point can be illuminated on the limbal area. In this case, the system may include a manipulator to allow the laser beam to be directed to a plurality of locations around the limbal area in succession to impact on a plurality of locations of the trabecular meshwork. A first point around the limbal area can be illuminated, after which, the laser beam can be directed towards a second point around the limbus, and so on. This can be done automatically and rapidly. Up to about 200 points can be illuminated simultaneously at the treatment intensity with a single laser.

Figure 6A:
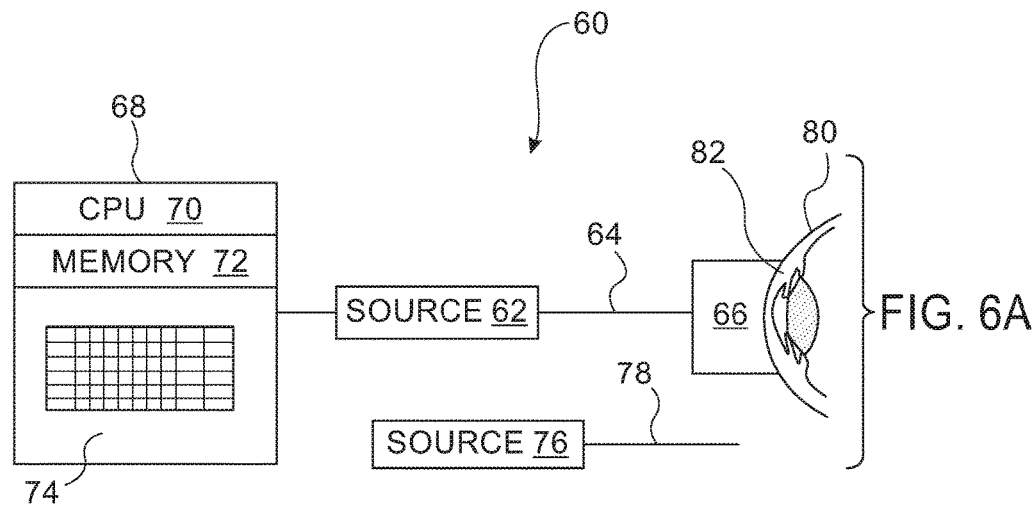
FIGS. 6A and 6B show systems for delivering electromagnetic radiation to a limbal area of an eye in accordance with embodiments of the invention.
Figure 6B:
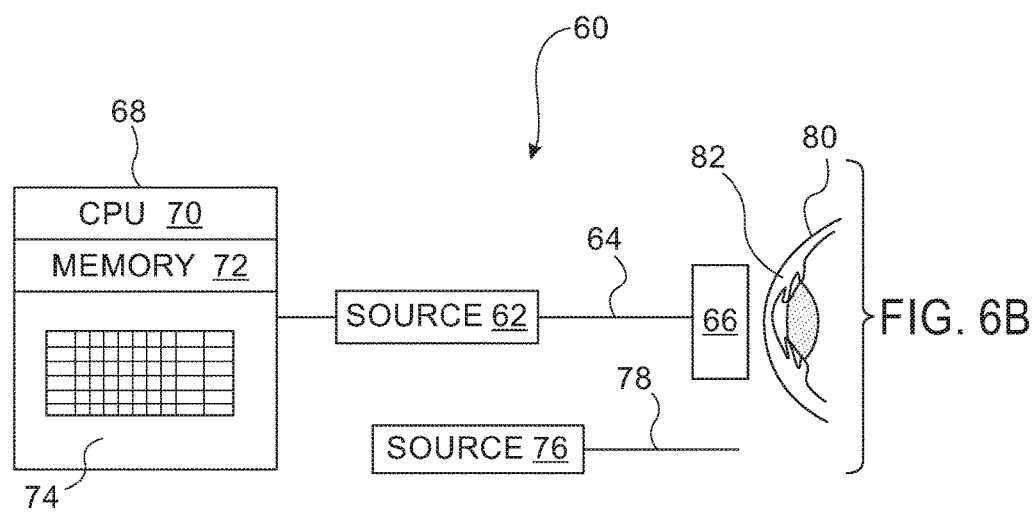

Turning now to FIGS. 6A and 6B, a system 60 of the present invention for use in treating an eye is schematically illustrated. The system 60 includes an illumination unit including a first source 62 of electromagnetic radiation that generates a treatment beam 64, and a second source 76 of electromagnetic radiation that generates an aiming beam. The system 60 also includes a beam shaping device 66 for shaping and directing the treatment beam 64 to one or more regions of a limbal area of an eye. The beam shaping device 66 may be, for example, any one of the mask-like devices 20, 24, 30 or may use a lens 40 described above. As previously mentioned, it should be noted that the device 66 need not be use in contact with the eye, but generally, as shown in the non-limiting example of FIG. 6A, it may be configured for direct contact with eye. FIG. 6B shows another non-limiting example in which device 66 is not in contact with the eye. Operation of the source 62 is under the control of a control unit 68 which is typically a computer device comprising inter alia a CPU 70, a memory 72 and a user input such as a keypad 74. The CPU 70 is installed with an electronic utility (software/hardware) pre-programmed according to the invention for receiving the user input indicative of that the aiming beam is properly aligned with the limbus for actuating the treatment mode of the system and controlling the pulse operation of the source 62 and possibly also rotation of the aperture disk. Also preferably provided in the system is a marker utility for marking a region onto which the patient's eye should be focused or in other words the line of sight of the patient should be directed to said region thus enabling to keep the patient's eye in a correct position during treatment. The marker may be constituted by a light spot aligned with the center of the beam shaping device (disk). To this end, the disk may be made of material opaque for both the aiming and treatment beams and in addition to the above-described optical windows transparent for the aiming and treatment beams around the periphery region thereof, has a central optical window transparent only for the aiming beam. Alternatively, alight spot may be projected onto the central region of the disk at its side facing the patient's eye. This may for example be implemented using the same aiming beam source, by splitting the emitted beam into two portions, one forming the aiming beam propagating towards one side of the disk, and the other being directed (by mirrors) towards the central region of the other side of the disk.

The treatment beam 64 can have a wavelength, for example, between 514 and 850 nm. The source 62 may be a laser operative in the near infrared range, such as a 532 Nd:YAG laser.

The user input device 74 may be used to input parameters relating to the treatment. For example, a user may input the beam intensity, the number of pulses of electromagnetic radiation that is to be delivered to the eye, and the pulse rate. The user selection of the beam shaping device for use in the treatment procedure determines a number of illuminated spots around the limbus. The parameters may be stored in the memory 72. The memory may also be used to store data relating to the individual being treated, as well as any relevant observations relating to the treatment.

Each pulse duration may be between 1 and 1000 milliseconds, and the fluence of a single pulse may be 0.5 to 1 J/cm$^2$. The total energy delivered to a single eye may be from 4 to 8 J. At this fluence, the beam 64 is not visible. The second source 76 of electromagnetic radiation produces a visible light beam 78. The source 76 (or appropriate light directing element) may be temporarily positioned to direct the beam 78 towards the eye via the device 66 while manipulating the position of the device 66 until arriving to the proper position of the device 66 and thus of the illumination pattern produced by the beam 78 as described above. The device 66 is properly positioned, whether the device is in contact with the eye or not, when the beam 78 impinging on the device 66 "draws" the lumbus area contour and thus the treatment beam 64 is delivered only to the limbal area 82 of the eye 80.

In use, the device 66 is positioned at a predetermined distance from the eye, the distance ranges between less than 1 mm to 200 mm. The aiming light source 76 is activated to illuminate, with the visible beam 78, an annulus having an inner (or outer) diameter that surrounds the limbus (as described above using opaque or transparent disk for visual radiation), and while under such illumination the source 62 is activated to generate a predetermined sequence of pulses of the treatment beam 64, hitting the eye within the defined annulus.

The sources of the aiming and treatment beams, 76 and 62 respectively, are preferably activated concurrently to make sure that the treatment beam is always directed to the right region(s) in the eye. At times, a sequence is actuated that includes sequential illumination by source 76 and treatment by source 62 to different spots in the limbal area of the eye each time. At any time, the device 66 may be rotated and another sequence of one or more pulses may be generated. The process may be repeated as required in any treatment. Once the patient's eye which is to be treated is positioned properly in the optical path of the beam and the line of sight of the patient is properly directed, the whole treatment procedure using the system of the present invention lasts for only part of a second, thus enhancing the patient convenience and supplying a very effective treatment.

The invention claimed is:

1. A method, comprising:
providing a system that comprises a laser source and a hardware-implemented beam-shaping device comprising one or more optical elements;
generating electromagnetic radiation by the laser source; and
irradiating one or more regions of a trabecular meshwork of an eye with the electromagnetic radiation generated by the laser source, by directing the electromagnetic radiation using the beam-shaping device through an entire thickness of a scleral limbus of the eye without any contact with the eye.

2. The method according to claim 1, wherein irradiating the trabecular meshwork with the electromagnetic radiation comprises treating glaucoma in the eye.

3. The method according to claim 1, wherein irradiating the trabecular meshwork with the electromagnetic radiation comprises treating open-angle, narrow-angle or closed-angle glaucoma in the eye.

4. The method according to claim 1, wherein directing of the electromagnetic radiation to the eye is performed not through a gonioscopic lens.

5. The method according to claim 1, wherein directing the electromagnetic radiation comprises irradiating, simultaneously or sequentially, multiple points distributed on the scleral limbus of the eye.

6. The method according to claim 1, wherein directing the electromagnetic radiation comprises irradiating multiple arch-shaped regions on the scleral limbus of the eye.

7. The method according to claim 1, wherein directing the electromagnetic radiation comprises irradiating multiple circular regions on the scleral limbus of the eye.

8. The method according to claim 1, wherein directing the electromagnetic radiation comprises guiding the electromagnetic radiation through multiple apertures in a fixture that is opaque to the electromagnetic radiation, wherein the apertures are aimed toward multiple regions of the trabecular meshwork.

9. The method according to claim 8, and comprising rotating the fixture, so as to direct the electromagnetic radiation to a first number of the regions that is larger than a second number of the apertures.

10. The method according to claim 1, wherein directing the electromagnetic radiation comprises guiding the electromagnetic radiation through an array of optical fibers whose ends are aimed toward multiple regions of the trabecular meshwork, without making contact with the eye.

11. The method according to claim 1, wherein directing the electromagnetic radiation comprises guiding the electromagnetic radiation using a refractive or diffractive optical element, without making contact with the eye.

12. The method according to claim 1, and comprising generating a visible aiming beam for aiming the electromagnetic radiation by an operator, wherein directing the electromagnetic radiation comprises guiding both the electromagnetic radiation and the aiming beam.

* * * * *